(12) United States Patent
Ruffer, Jr.

(10) Patent No.: US 9,517,651 B2
(45) Date of Patent: Dec. 13, 2016

(54) DEVELOPER FOR THERMAL RECORDING MEDIA AND THERMAL COMPOSITION MEDIA USING THE SAME

(71) Applicant: Ronald Q. Ruffer, Jr., Sinking Spring, PA (US)

(72) Inventor: Ronald Q. Ruffer, Jr., Sinking Spring, PA (US)

(73) Assignees: Performance Chemicals, Inc., Sinking Spring, PA (US); Marubeni Specialty Chemicals, Inc., White Plains, NY (US)

( * ) Notice: Subject to any disclaimer, the term of this patent is extended or adjusted under 35 U.S.C. 154(b) by 0 days.

(21) Appl. No.: 14/865,405

(22) Filed: Sep. 25, 2015

(65) Prior Publication Data
US 2016/0089919 A1 Mar. 31, 2016

Related U.S. Application Data

(60) Provisional application No. 62/055,932, filed on Sep. 26, 2015.

(51) Int. Cl.
*B41M 5/333* (2006.01)
*B41M 5/327* (2006.01)
*B41M 5/337* (2006.01)
*C07C 275/36* (2006.01)

(52) U.S. Cl.
CPC ......... *B41M 5/3335* (2013.01); *B41M 5/3275* (2013.01); *B41M 5/3336* (2013.01); *B41M 5/3372* (2013.01); *B41M 5/3375* (2013.01); *B41M 5/3377* (2013.01); *C07C 275/36* (2013.01); *B41M 2205/04* (2013.01); *B41M 2205/28* (2013.01)

(58) Field of Classification Search
CPC ..... B41M 5/327; B41M 5/3275; B41M 5/333; B41M 5/3333; B41M 5/3335; B41M 5/337; B41M 5/3372
USPC .................................................. 503/216, 217
See application file for complete search history.

(56) References Cited

U.S. PATENT DOCUMENTS

| | | | |
|---|---|---|---|
| 5,470,816 A | 11/1995 | Satake et al. | 503/201 |
| 5,498,772 A | 3/1996 | Maruyama et al. | 503/216 |
| 5,656,569 A | 8/1997 | Takano et al. | 503/216 |
| 5,811,369 A | 9/1998 | Nagai et al. | 503/209 |
| 6,596,669 B1 | 7/2003 | Maruyama et al. | 503/204 |
| 6,890,881 B2 | 5/2005 | Tsukada | 503/216 |
| 6,927,007 B2 | 8/2005 | Takeuchi | 430/138 |
| 7,192,904 B2 | 3/2007 | Iwasaki et al. | 503/216 |
| 2009/0009577 A1 | 1/2009 | Nigam | 347/105 |
| 2009/0048106 A1 | 2/2009 | Shimbo | 503/201 |
| 2011/0287930 A1 | 11/2011 | Ochiai | 503/200 |

OTHER PUBLICATIONS

International Search Report PCT/US15/52303.

*Primary Examiner* — Bruce H Hess
(74) *Attorney, Agent, or Firm* — Alvin T. Rockhill

(57) ABSTRACT

The subject invention more specifically discloses compounds which are particularly useful as a developer for thermal recording media. These compounds include p-(p-{3-[p-(p-hydroxyphenoxy)phenyl]ureido}phenoxy)phenol, m-(p-{3-[p-(p-hydroxyphenoxy)phenyl]ureido}phenoxy) phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol. The present invention also reveals a thermal recording sheet having a thermal recording layer containing a colorless or pale colored dye precursor and a color developer reactable with said dye precursor upon heating to develop a color, wherein said color developer is a compound selected from the group consisting of p-(p-{3-[p-(p-hydroxyphenoxy)phe-
(Continued)

nyl]ureido}phenoxy)phenol, m-(p-{3-[p-(p-hydroxyphenoxy)phenyl]ureido}phenoxy)phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol.

34 Claims, 2 Drawing Sheets

DEVELOPER FOR THERMAL RECORDING MEDIA AND THERMAL COMPOSITION MEDIA USING THE SAME

This application claims the benefit of U.S. Provisional Patent Application Ser. No. 62/055,932, filed on Sep. 26, 2014. The teachings of U.S. Provisional Patent Application Ser. No. 62/055,932 are incorporated herein by reference in their entirety.

BACKGROUND OF THE INVENTION

In general, to obtain a thermal recording sheet, a colorless or pale colored electron-donating dye and a color developer (an electron accepting material), such as a phenolic compound, are individually pulverized to fine particles, mixed with each other, and a binder, a filler, a sensitizer, a slip agent, and other additives are added to obtain a coating color, which is coated on a substrate such as paper, synthetic paper, films, plastics, or the like. The coated sheet is color developed through an essentially instantaneous chemical reaction which is induced by heating with a thermal head, a hot stamp, laser light, or the like to obtain a visible record. The thermal recording sheet can be used in a wide variety of applications, such as measuring recorders, terminal printers for computers, facsimile machines, automatic ticket vending machines, bar-code labeling equipment, and the like.

Urea compounds are well known as electron accepting materials which are commonly used as developers in thermal recording media. U.S. Pat. Nos. 5,470,816, 5,656,569, 5,811,369, and 6,927,007 describe thermal recording media which can include such urea compounds. In any case, the thermal recording media should include a developer which allows for high efficiency and good reactivity while meeting additional desired properties which can include appropriate thermal response, heat resistance, water resistance, oil resistance, plasticizer resistance, and low background color.

SUMMARY OF THE INVENTION

The present invention relates to a novel developers that combine the known attributes of a urea compound and the known attributes of hydroxyl-terminated phenyl compounds (such as 2,2-bis(p-hydroxyphenyl)propane, or bisphenol A; bis(4-hydroxyphenyl)methane, or bisphenol F; and 4-Hydroxyphenyl sulfone, or bisphenol S) with those of ether compounds, such as 4-hydroxyphenyl 4-isoprooxyphenylsulfone (commonly known as D-8) and 4[4'-{(1'methylethyloxy)phenyl]sulfonyl]phenol (commonly known as D-90) to create a novel and useful thermal developer for use in heat sensitive recording paper. The developers of this invention have chemical structures which include multiple electron accepting sites which allows for high efficiency and good reactivity without compromising other desired properties including appropriate thermal response, heat resistance, water resistance, oil resistance, plasticizer resistance and low background color. The developers of this invention have characteristics which make them particularly desirable for use in thermal recording media which is utilized in conjunction with heat sensitive paper, such as the heat sensitive paper which is typically used for tags, tickets, and labels. In any case, thermal recording media made with the developers of this invention can be used on a wide variety of substrates including, but not limited to, paper, metal, plastics, metallic film, synthetic film, woven fabrics, and non-woven fabrics. For instance, the synthetic films used as the substrate can be comprised of a polyolefin, such as polyethylene or polypropylene; a vinyl polymer, such as polyvinyl chloride; polycarbonate; a polyester, such as polyethylene terephthalate or polyethylene naphthalate; or a polyamide, such a nylon-6,6.

The subject invention more specifically discloses compounds which are particularly useful as a developer for thermal recording media. These compounds include p-(p-{3-[p-(p-hydroxyphenoxy)phenyl]ureido}phenoxy)phenol, m-(p-{3-[p-(p-hydroxyphenoxy)phenyl]ureido}phenoxy)phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol.

The present invention also reveals a thermal recording sheet having a thermal recording layer containing a colorless or pale colored dye precursor and a color developer reactable with said dye precursor upon heating to develop a color, wherein said color developer is a compound selected from the group consisting of p-(p-{3-[p-(p-hydroxyphenoxy)phenyl]ureido}phenoxy)phenol, m-(p-{3-[p-(p-hydroxyphenoxy)phenyl]ureido}phenoxy)phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol.

The subject invention also discloses a thermal recording medium which is comprised of a substrate having thereon a recording layer containing a colorless or pale colored dye precursor and a color developer reactable with said dye precursor upon heating to develop a color, wherein said color developer is a compound selected from the group consisting of p-(p-{3-[p-(p-hydroxyphenoxy)phenyl]ureido}phenoxy)phenol, m-(p-{3-[p-(p-hydroxyphenoxy)phenyl]ureido}phenoxy)phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol.

DETAILED DESCRIPTION OF THE INVENTION

Figure 1:
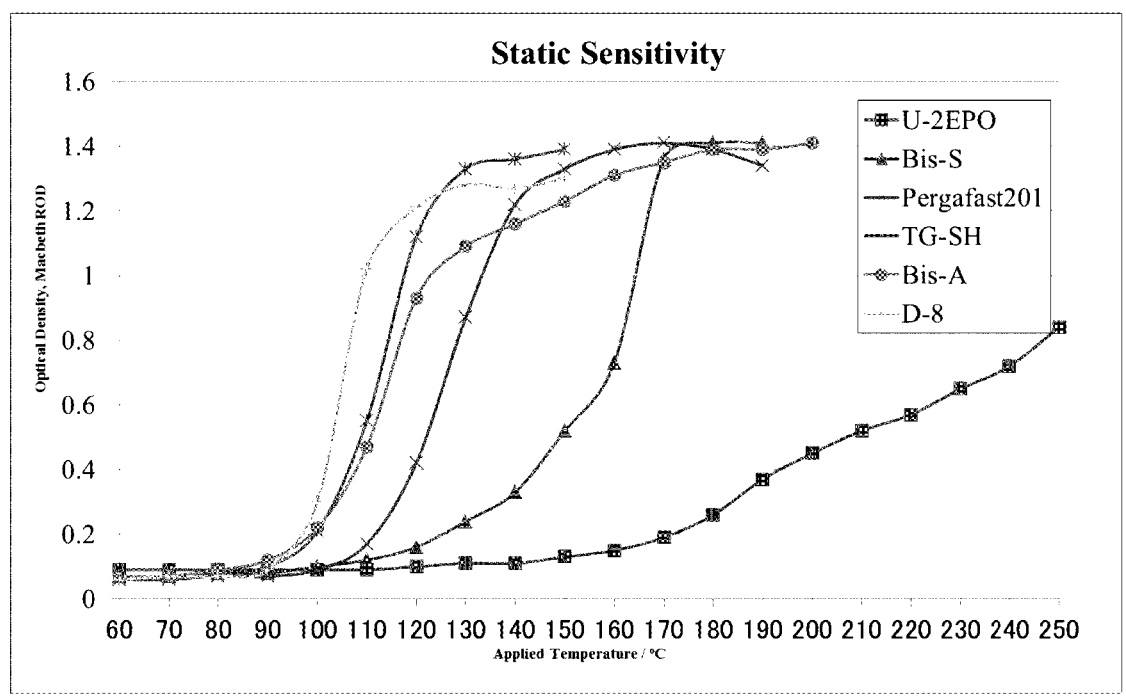
FIG. 1 is a graph which illustrates the results of the static sensitivity testing done in Example 2.

The IUPAC name of a preferred developer of this invention p-(p-{3-[p-(p-hydroxyphenoxy)phenyl]ureido}phenoxy)phenol which is also known as: 1,3-bis(4-(4-hydroxyphenoxy)phenyl)urea. This compound is of the structural formula:

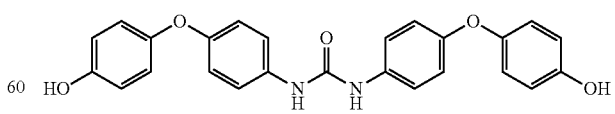

Various isomers of p-(p-{3-[p-(p-hydroxyphenoxy)phenyl]ureido}phenoxy)phenol are also useful as developers in conjunction with this invention. For instance, one or both hydroxyl groups can be present on the hydroxyphenoxy structure in the ortho or meta positions relative to the ether linkage, such as m-(p-{3-[p-(p-hydroxyphenoxy)phenyl]ureido}phenoxy)phenol; which is of the structural formula:

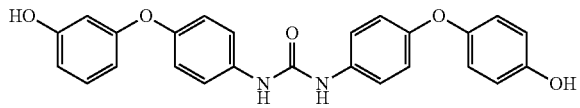 [SMILES: O=C(Nc1ccc(Oc2ccc(O)cc2)cc1)Nc1ccc(Oc2cccc(O)c2)cc1]

and o-(p-{3-[p-(p-ydroxyphenoxy)phenyl]ureido}phenoxy)phenol; which is of the structural formula:

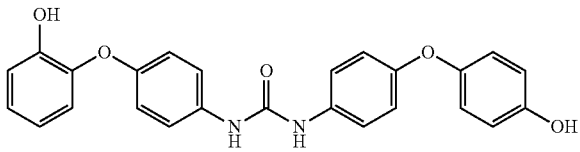 [SMILES: O=C(Nc1ccc(Oc2ccc(O)cc2)cc1)Nc1ccc(Oc2ccccc2O)cc1]

In another embodiment of this invention the ether linkage can be present in the ortho or meta positions relative to the urea linkage. Examples of such isomers include p-(p-{3-[m-(p-hydroxyphenoxy)phenyl]ureido}phenoxy)phenol; which is of the structural formula:

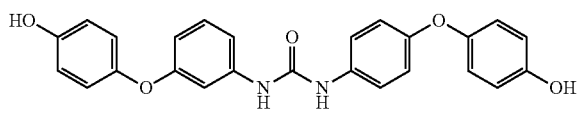 [SMILES: O=C(Nc1ccc(Oc2ccc(O)cc2)cc1)Nc1cccc(Oc2ccc(O)cc2)c1]

and p-(m-{3-[o-(p-Hydroxyphenoxy)phenyl]ureido}phenoxy)phenol, which is of the structural formula:

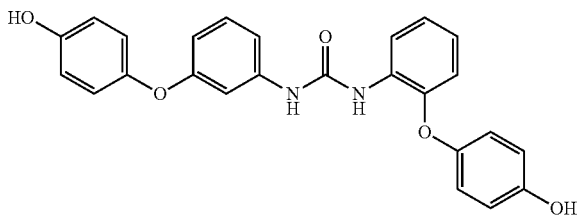 [SMILES: O=C(Nc1cccc(Oc2ccc(O)cc2)c1)Nc1ccccc1Oc1ccc(O)cc1]

It should be further noted that any and all combinations of the above delineated isomers can be used as the developer of this invention. It should be further noted that the novel developers of this invention (any combination of isomers) can be used in developer formulations as a major or minor constituent of the total developer in combination with conventional developers in the thermal recording medium. In other words, the novel developers of this invention can be used alone or in combination other developers either as a major or minor constituent of the total developer quantity. For instance, the developers of this invention can be used in combination with other known electron accepting such as:
2,4'-Dihydroxydiphenylsulfone (CAS#5397-34-2),
4,4'-Dihydroxydiphenylsulfone (CAS#80-90-1),
Bis-(3-allyl-4-hydroxyphenyl)sulfone (CAS#41481-66-7),
4-[4'-[(1'-methylethyloxy)phenyl]sulfonyl]phenol (CAS#191680-83-8),
4-hydroxyphenyl 4-isoprooxyphenylsulfone (CAS#95235-30-6),
N-(p-Toluenesulfonyl)-N'-(3-p-toluenesulfonyloxyphenyl) urea (CAS#232938-43-1),
Phenol, 4-[4-(2-propen-1yloxy)phenyl]sulfonyl (CAS#97042-18-7),
4-Hydroxy-4'benzyloxydiphenylsulfone (CAS#63134-33-8), and
4,4'bis(N-carbamoyl-4-methylbenzenesulfonamide)diphenylmethane (CAS#151882-81-4).

The developers of this invention can also be utilized in thermal recording media in combination with one or more of the developers disclosed in U.S. Pat. Nos. 5,470,816, 5,656,569, 5,811,369, and 6,927,007. The teachings of U.S. Pat. Nos. 5,470,816, 5,656,569, 5,811,369, and 6,927,007 are incorporated herein by reference for the purpose of disclosing such developers.

The novel developer can to be used in combination with a colorless electron donating dye in order to facilitate image formation. Examples of these dyes include: 2-anilino-3-methyl-6-diethylaminofluorane, 2-anilino-3-methyl-6-dibutylaminofluorane, 2-anilino-3-methyl-6-(N-ethyl-N-isoamylamino)fluorine, 2-anilino-3-methyl-6-(N-ethyl-N-propylamino)fluorane, 2-anilino-3-methyl-6-di-n-amylaminofluorane, 2-anilino-3-methyl-6-(N-ethyl-N-p-tolylamino)fluorane, 2-anilino-3-methyl-6-N-ethyl-N-sec-butylaminofluorane, 3-di-(n-pentylamino)-6-methyl-7-anilinofluorane, 3-(N-isoamyl-N-ethylamino)-6-methyl-7-anilinofluorane, 3-(N-n-hexyl-N-ethylamino)-6-methyl-7-anilinofluorane, 3-[N-(3-ethoxypropyl)-N-ethylamino]-6-methyl-7-anilinofluorane, 3-di-(n-butylamino)-7-2-chloroanilino)fluorane, 3-diethylamino-7-(2-chloroanilino)fluorane, 3-(N-cyclohexyl-N-methylamino)-6-methyl-7-anilinofluorane, and the like. These dyes can be used solely or in combination of two or more other dyes in a single heat-sensitive recording layer as disclosed in U.S. Pat. No. 7,192,904. The teachings of U.S. Pat. No. 7,192,904 are incorporated herein by reference for the purpose of disclosing dyes and combinations of dyes that can be utilized in thermal recording media in conjunction with the developers of this invention.

A sensitizer may be used in combination with the developer and electron donating colorless dye for the purposes of improving image stability, density, and modifying the temperature at which the image forms. These materials can be used either alone or in combination with one another. Examples of such sensitizers include stearamide, N-hydroxymethylstearamide, N-stearylstearamide, ethylenebisstearamide, N-stearylstearamide, ethylenebisstearamide, N-stearylurea, benzyl-2-naphthyl ether, m-terpphenyl, 4-benzylbiphenyl, 4-acetylbiphenyl, 4-(4-methylphenoxy) biphenyl, 1,2-bis(3-methylphenoxy)ethane, 1,2-diphenoxyethane, 2,2'-bis(4-methoxyphenoxy)diethyl ether, diphenoxyxylene, bis(4-methoxyphenyl)ether, diphenyl adipate, dibenzyl oxalate, di(4-methylbenzyl)oxalate, di(4-chlorobenzyl)oxalate, dimethyl terephthalate, dibenzyl terephthalate, phenyl benzene sulfonic ester, diphenylsulfone, bis(4-allyloxyphenyl) sulfone, 4-acetylacetophenone, acetoacetic acid anilides, fatty acid aniliides, etc. The teachings of U.S. Pat. No. 6,890,881 B2 are incorporated herein by reference for the purpose of disclosing sensitizers and combinations of sensitizers that can be utilized in thermal recording media in conjunction with the developers of this invention.

In manufacturing thermal recording media the above-referenced materials are typically combined ground together in a mill to a fine particle size, using binders, such as polyvinyl alcohol (anionic grades such as sulfonated polyvinyl alcohol are particularly useful; low hydrolysis grades are also preferred) and/or surfactants. Often other materials are also added into the mixture to be milled (though these can also be added post-milling stage): additional binders such as polyvinyl alcohol, modified polyvinyl alcohol, acrylic emulsions, styrene copolymer emulsions, butadiene copolymer emulsions, acrylonitrile copolymer and terpolymer emulsions, polyvinyl acetate emulsions, vinyl acetate ethylene emulsions, polyurethane emulsions, starches, hydroxymethyl cellulose and other synthetic and natural binders; this is then combined with fillers such as titanium dioxide, silica, aluminum tri-hydrate, clay, mica, calcium carbonate, talc, magnesium hydroxide, magnesium oxide, etc; synthetic fillers such as hollow plastic spheres, polystyrene or polypropylene beads, can also be utilized in this application.

Other ingredients such as slip agents (zinc stearate, calcium stearate, stearamide, polyethylene wax, surfactants, etc.), UV absorbers and optical brighteners are also commonly added to improve the mechanical and physical characteristics of the coating and the finished product.

Especially in the case of tag, ticket and label applications, a protective coating designed to improve the stability of the image under exposure to water, moisture, oil (and other organic solvents) and/or grease is especially important. This is typically applied on top of the layer that contains the developer and color former. Commonly used coatings include products, such as carboxylated polyvinyl alcohol (cross-linked or non-crosslinked), acetoacetylated polyvinyl alcohols (also with and without crosslinking), standard unmodified polyvinyl alcohols (fully hydrolyzed, high molecular weight grades preferred), starches, acrylic emulsions, polyurethane emulsions, etc. This layer may also contain fillers as mentioned above.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this experiment, 1,3-bis(4-(4-hydroxyphenoxy)phenyl)urea was synthesized utilizing a three step procedure. In the first step of this procedure ethyl(4-(4-methoxyphenoxy)phenyl)carbamate was synthesized by reacting 4-(4-methoxyphenoxy)aniline in the presence of pyridine and ethyl chloroformate according to the following reaction:

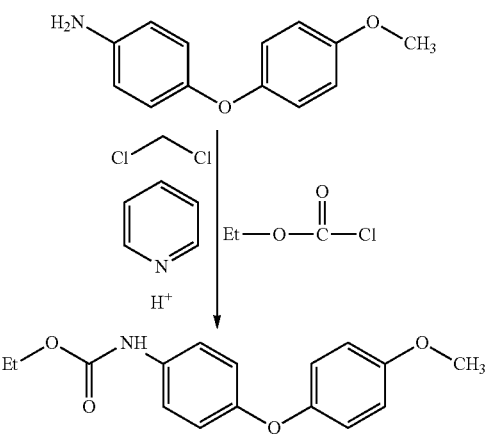

In the procedure used 23.7 mmol of starting material, 100 ml of DCM and 46.5 mmol of pyridine were combined in a round bottom flask and cooled to a temperature of 0° C. Then 34.8 mmol of ethyl chloroformate was added drop wise over time and maintained at a temperature of 0° C. Then the reaction product was quenched with hydrochloric acid (HCl), dried, concentrated, washed with hexanes solvent, and dried. In this step of the procedure a yield of about 94 percent was attained.

In the second step of the procedure was then carried out according to the following reaction scheme where 1,3-bis (4-(4-Methoxyphenoxy)phenyl)urea was made from ethyl (4-(4-Methoxyphenoxy)phenyl)carbamate and 4-(4-Methoxyphenoxy)aniline in the presence of toluene and trimethyl aluminum:

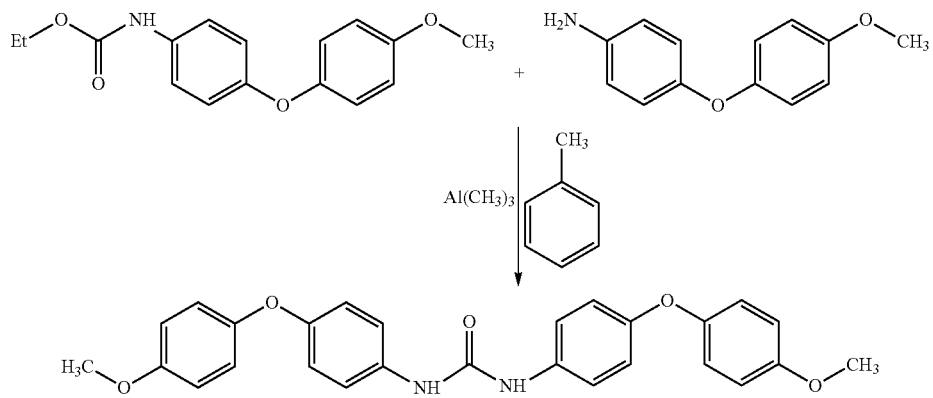

In this step of the procedure 4-(4-methoxyphenoxy)aniline was dissolved in toluene (1:25 in toluene) and cooled to a temperature −5° C. Trimethyl aluminum (AlCH$_3$)$_3$ was then added over time under positive nitrogen (N$_2$) pressure with a significant exotherm being experienced). Ethyl(4-(4methoxyphenoxy)phenyl)carbamate was then added as a solid in small portions and heated to a temperature of 80° C. for 8 hours. It was then cooled and quenched with hydrochloric acid (HCl). This step was conducted using caution because the hydrochloric acid generates a significant exothermic reaction and gas formation. The resulting paste was filtered, rinsed with ether and water and was then dried under vacuum with a yield of 79% being attained.

The following reaction was carried out as the third and final step of the synthesis procedure wherein the 1,3-bis(4-(4-hydroxyphenoxy)phenyl)urea (U-2EPO) was made from 1,3-bis(4-(4-methoxyphenoxy)phenyl)carbamate in dichloromethane and tetrabromoborane ($BBr_3$):

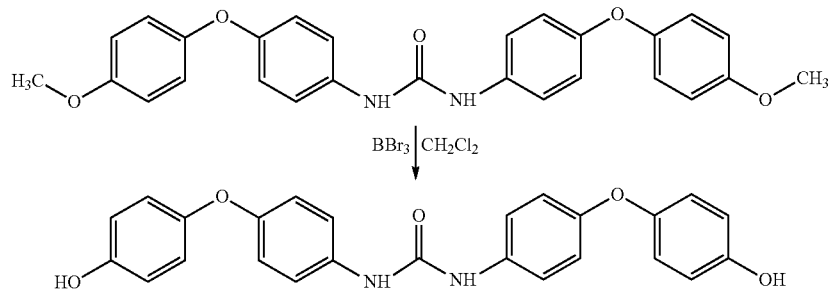

In this step of the synthesis procedure 1,3-bix(4-(4-(methoxyphenoxy)phenyl)urea was added to $CH_2Cl_2$ though it did not dissolved; the material appeared to dissolve as $BBr_3$ was added under a positive nitrogen ($N_2$) atmosphere over time with the reaction being moderately exothermic. The mixture was allowed to reach a temperature of 15° C. and was then cooled to a temperature of 0° C. and quenched with water (very exothermic). The resulting pasty solids were filtered and again washed with water until a neutral pH was attained. The paste was then washed with ether and dried with a yield of 57% being attained.

EXAMPLE 2

In this experiment a coating solution for heat-sensitive recording layers was made using the U-2EPO synthesized in Example 1 as a developer. The properties of the heat-sensitive recording layer made using the U-2EPO as the developer were then compared to those of heat-sensitive recording layers made utilizing a number of conventional developers. In the procedure used a first liquid dispersion (Liquid A) was made by pulverizing and dispersing 25 parts by weight of 3-dibutylamino-6-methyl-7-anilino-fluorane (ODB-2), 25 parts by weight of a 20% aqueous sulfonated polyvinyl alcohol solution (Gohsenx™ L-3266 sulfonated polyvinyl alcohol from the Nippon Synthetic Chemical Industry Co. Ltd.), and 50 parts by weight of water for 12 hours using a sand grinder. A second liquid dispersion (Liquid B) was made by pulverizing and dispersing 25 parts by weight of the developer identified in Table 1, 25 parts by weight of the 20% aqueous sulfonated polyvinyl alcohol solution and 50 parts by weight of water for 1 hour in the sand grinder. Then, color developing solutions were prepared by mixing 24 parts by weight of the first liquid dispersion (Liquid A), 8.6 parts by weight of the second liquid dispersion (Liquid B), 9.0 parts by weight of a 67% aqueous calcium carbonate solution, 6.3 parts by weight of a 48% aqueous styrene-butadiene copolymer latex solution, and 52.1 parts by weight of water.

A coating solution for a protective layer was made by mixing 165 parts by weight of a 40% aqueous solution of a styrene-acrylic copolymer emulsion, 100 parts by weight of a 39% aqueous solution of zinc stearate, and 15 parts by weight of a 67% solution of calcium carbonate.

The color developing solutions and the coating solution for the protective layer were then successively applied to supports (neutralized paper) using a wire bar. The color developing solutions were applied at a solids level of 4.6 g/m² and the solution for the protective layer was applied at a solids level of 2.0 g/m². The coated supports were dried at a temperature of 50-55° C. for 5 minutes to produce the heat-sensitive recording materials which were subsequently tested to determine static sensitivity, dynamic sensitivity, image stability, and back ground stability.

Static sensitivity was determined using a Toyo Seiki Heat Gradient HG-100-2 tester with the recording material being developed under a pressure of 1.0 kg/m² which was applied for 5 seconds at over a temperature range of 60° C. to 250° C. The image density obtained by the development was measured using a SpectroEye® colorimetric system manufactured by X-Rite Co., Ltd. The results of this static sensitivity testing is shown in Table 1 and is illustrated in graphical from in FIG. 1.

TABLE 1

| Temperature | U-2EPO | Bis-S | Pergafast® 201 | TG-SH | Bis-A | D-8 |
|---|---|---|---|---|---|---|
| 250° C. | 0.84 | | | | | |
| 240° C. | 0.72 | | | | | |
| 230° C. | 0.65 | | | | | |
| 220° C. | 0.57 | | | | | |
| 210° C. | 0.52 | | | | | |
| 200° C. | 0.45 | | | | 1.41 | |
| 190° C. | 0.37 | 1.41 | 1.34 | | 1.39 | |
| 180° C. | 0.26 | 1.41 | 1.39 | | 1.39 | |
| 170° C. | 0.19 | 1.36 | 1.41 | | 1.35 | |
| 160° C. | 0.15 | 0.73 | 1.39 | | 1.31 | |
| 150° C. | 0.13 | 0.52 | 1.33 | 1.39 | 1.23 | 1.3 |
| 140° C. | 0.11 | 0.33 | 1.22 | 1.36 | 1.16 | 1.27 |
| 130° C. | 0.11 | 0.24 | 0.87 | 1.33 | 1.09 | 1.28 |
| 120° C. | 0.1 | 0.16 | 0.42 | 1.12 | 0.93 | 1.21 |
| 110° C. | 0.09 | 0.12 | 0.17 | 0.55 | 0.47 | 1.02 |
| 100° C. | 0.09 | 0.1 | 0.09 | 0.21 | 0.22 | 0.3 |
| 90° C. | 0.09 | 0.08 | 0.07 | 0.1 | 0.12 | 0.09 |
| 80° C. | 0.09 | 0.08 | 0.07 | 0.08 | 0.09 | 0.07 |
| 70° C. | 0.09 | 0.07 | 0.06 | 0.07 | 0.07 | 0.07 |
| 60° C. | 0.09 | 0.07 | 0.06 | 0.07 | 0.07 | 0.06 |

The developers evaluated in this series of experiments included the following:
U-2EPO=1,3-bis(4-(4-hydroxyphenoxy)phenyl)urea
Bis-S=4-hydroxyphenyl sulfone (Bisphenol S)
Pergafast® 201=non-phenolic color developer from BASF
TG-SH=3,3'-diallyl-4,4'-dihydroxy-diphenyl sulfone
Bis-A=2,2-bis(p-hydroxyphenyl) propane (Bisphenol A)
D-8=4-hydroxyphenyl 4-isprooxyphenylsulfone As can be seen from reviewing the data in Table 1 and viewing FIG. 1, the static sensitivity testing showed that the coated support made using the U-2EPO developer of this invention had characteristics which were much better for high temperature applications than conventional developers. As can be seen, as temperatures were increased above 110° C. the difference in static sensitivity attained with the U-2EPO developer and the conventional developers became more pronounced with this difference being very dramatic over the temperature range of 150° C. to 180° C.

Dynamic sensitivity was determined using a Okura Engineering TH-M2/PP tester utilizing a printing voltage of 16.0 volts, a line period of 1.6 msec, and a pulse width of 0.50-1.40 mm/sec with the image density obtained by the development being measured with the SpectroEye® colorimetric system manufactured by X-Rite Co., Ltd. The results of this dynamic sensitivity testing is reported in Table 2 and is illustrated in graphical from in FIG. 2.

TABLE 2

| Pulse Width (mm/sec) | U-2EPO | Bis-S | Pergafast201 | TG-SH | Bis-A | D-8 |
|---|---|---|---|---|---|---|
| 1.40 | 0.88 | 1.29 | 1.21 | 1.25 | 1.26 | 1.21 |
| 1.30 | 0.77 | 1.28 | 1.21 | 1.30 | 1.28 | 1.21 |
| 1.20 | 0.62 | 1.14 | 1.19 | 1.30 | 1.28 | 1.23 |
| 1.10 | 0.45 | 0.97 | 1.12 | 1.24 | 1.18 | 1.26 |
| 1.00 | 0.31 | 0.64 | 0.93 | 1.07 | 0.99 | 1.11 |
| 0.90 | 0.19 | 0.43 | 0.61 | 0.79 | 0.77 | 0.93 |
| 0.80 | 0.11 | 0.26 | 0.37 | 0.49 | 0.54 | 0.64 |
| 0.70 | 0.09 | 0.13 | 0.19 | 0.30 | 0.31 | 0.34 |
| 0.60 | 0.08 | 0.08 | 0.09 | 0.15 | 0.17 | 0.17 |
| 0.50 | 0.08 | 0.07 | 0.07 | 0.08 | 0.08 | 0.07 |

Figure 2:
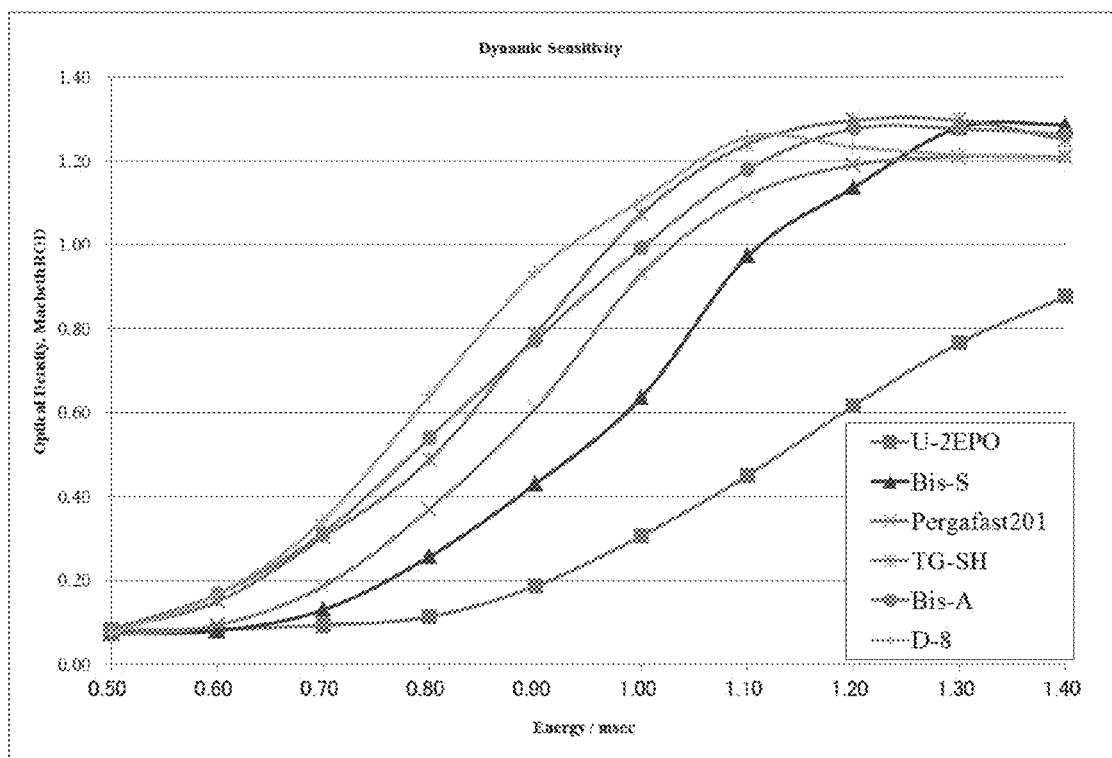
FIG. 2 is a graph which illustrates the results of the dynamic sensitivity testing done in Example 2.

As can be seen from reviewing the data in Table 2 and the viewing FIG. 2, the dynamic sensitivity testing showed that the coated support made using the U-2EPO developer of this invention had characteristics which were much better for high temperature applications than conventional developers. As can be seen, as energy levels were increased above a pulse width of about 0.7 mm/sec this difference became more evident. The difference between the U-2EPO developer of this invention and the conventional developers was very apparent at energy levels over about 0.80 mm/sec and particularly within the range of 0.90 mm/sec to 1.20 mm/sec.

Image stability was evaluated utilizing an accelerated aging test procedure. In this procedure samples of the material were evaluated for density in the recorded area before storage and after (1) being stored soaked in water for 24 hours, (2) being aged in hot water at 60° C. for 24 hours, (3) being heated to 90° C. for 1 hour, and (4) being held at 80% relative humidity at 50° C. for 24 hours. Image density was again determined with the SpectroEye® colorimetric system.

The back-ground stability of the heat-sensitive recording materials was determined by aging the recording materials before recoding under the conditions used in the image stability testing with the density in the background area of the samples being measured before and after the aging procedures. Image density was again determined with the SpectroEye® colorimetric system. The image stability and back-ground stability of the samples is reported in Table 3.

TABLE 3

| | | Image stability (Survival rate) | | | | Background stability ISO Whitness/amount of change | | | | | |
|---|---|---|---|---|---|---|---|---|---|---|---|
| Developer | Back-ground ISO Whitness | Water Dip × 24 Hr | Heat 60° C. × 24 Hr | Heat 90° C. × 1 Hr | Heat & Moist 50° C. × 80% RH × 24 Hr | Heat 60° C. × 24 Hr | | Heat 90° C. × 1 Hr | | Heat & Moist 50° C. × 80% RH × 24 Hr | |
| U-2EPO | 62.1 | 84% | 94% | 80% | 88% | 57.1 | 5 | 58.4 | 3.7 | 58.1 | 4 |
| Bis-S | 70.1 | 84% | 102% | 103% | 103% | 64.7 | 5.4 | 55.4 | 14.7 | 64.9 | 5.2 |
| Pergafast201 | 75.1 | 84% | 102% | 102% | 98% | 70.3 | 4.8 | 59.2 | 15.9 | 68.8 | 6.3 |
| TG-SH | 71.2 | 84% | 103% | 106% | 99% | 61.0 | 10.2 | 43.8 | 27.4 | 64.0 | 7.2 |
| Bis-A | 71.7 | 49% | 105% | 113% | 103% | 63.6 | 8.1 | 29.6 | 42.1 | 59 | 12.7 |
| D-8 | 75.7 | 77% | 104% | 107% | 99% | 72.7 | 3 | 49.2 | 26.5 | 71.4 | 4.3 |

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A compound which is particularly useful as a developer for thermal recording media, said compound being selected from the group consisting of p-(p-{3-[p-(p-hydroxyphenoxy)phenyl]ureido}phenoxy)phenol, m-(p-{3-[p-(p-hydroxyphenoxy)phenyl]ureido}phenoxy)phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol.

2. The compound of claim 1 wherein said compound is p-(p-{3-[p-(p-hydroxyphenoxy)phenyl]ureido}phenoxy)phenol.

3. The compound of claim 1 wherein said compound is m-(p-{3-[p-(p-hydroxyphenoxy)phenyl]ureido}phenoxy)phenol.

4. The compound of claim 1 wherein said compound is o-(p-{3-[p-(p-hydroxyphenoxy)phenyl]ureido}phenoxy)phenol.

5. The compound of claim 1 wherein said compound is p-(p-{3-[m-(p-hydroxyphenoxy)phenyl]ureido}phenoxy)phenol.

6. The compound of claim 1 wherein said compound is p-(m-{3-[o-(p-hydroxyphenoxy)phenyl]ureido}phenoxy)phenol.

7. A thermal recording sheet having a thermal recording layer containing a colorless or pale colored dye precursor and a color developer reactable with said dye precursor upon heating to develop a color, wherein said color developer is a compound selected from the group consisting of p-(p-{3-

[p-(p-hydroxyphenoxy)phenyl]ureido}phenoxy)phenol, m-(p-{3-[p-(p-hydroxyphenoxy)phenyl]ureido}phenoxy)phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol.

8. The thermal recording sheet of claim 7 which is further comprised of an electron accepting material selected from the group consisting of 2,4'-Dihydroxydiphenylsulfone (CAS#5397-34-2), 4,4'-Dihydroxydiphenylsulfone (CAS#80-90-1), Bis-(3-allyl-4-hydroxyphenyl)sulfone (CAS#41481-66-7), 4-[4'-[(1'-methylethyloxy)phenyl]sulfonyl]phenol (CAS#191680-83-8), 4-hydroxyphenyl 4-isoprooxyphenylsulfone (CAS#95235-30-6), N-(p-Toluenesulfonyl)-N'-(3-p-toluenesulfonyloxyphenyl)urea (CAS#232938-43-1), Phenol, 4-[[4-(2-propen-1yloxy)phenyl]sulfonyl (CAS#97042-18-7), 4-Hydroxy-4'benzyloxydiphenylsulfone (CAS#63134-33-8), and 4,4'bis(N-carbamoyl-4-methylbenzenesulfonamide)diphenylmethane (CAS#151882-81-4).

9. The thermal recording sheet of claim 7 wherein the colorless or pale colored dye precursor is selected from the group consisting of 2-anilino-3-methyl-6-diethylaminofluorane, 2-anilino-3-methyl-6-dibutylaminofluorane, 2-anilino-3-methyl-6-(N-ethyl-N-isoamylamino)fluorine, 2-anilino-3-methyl-6-(N-ethyl-N-propylamino)fluorane, 2-anilino-3-methyl-6-di-n-amylaminofluorane, 2-anilino-3-methyl-6-(N-ethyl-N-p-tolylamino)fluorane, 2-anilino-3-methyl-6-N-ethyl-N-sec-butylaminofluorane, 3-di-(n-pentylamino)-6-methyl-7-anilinofluorane, 3-(N-isoamyl-N-ethylamino)-6-methyl-7-anilinofluorane, 3-(N-n-hexyl-N-ethylamino)-6-methyl-7-anilinofluorane, 3-[N-(3-ethoxypropyl)-N-ethylamino]-6-methyl-7-anilinofluorane, 3-di-(n-butylamino)-7-2-chloroanilino)fluorane, 3-diethylamino-7-(2-chloroanilino)fluorane, and 3-(N-cyclohexyl-N-methylamino)-6-methyl-7-anilinofluorane.

10. The thermal recording sheet of claim 7 which is further comprised of a sensitizer.

11. The thermal recording sheet of claim 10 wherein the sensitizer is selected from the group consisting of stearamide, N-hydroxymethylstearamide, N-stearylstearamide, ethylenebisstearamide, N-stearylstearamide, ethylenebisstearamide, N-stearylurea, benzyl-2-naphthyl ether, m-terpphenyl, 4-benzylbiphenyl, 4-acetylbiphenyl, 4-(4-methylphenoxy)biphenyl, 1,2-bis(3-methylphenoxy) ethane, 1,2-diphenoxyethane, 2,2'-bis(4-methoxyphenoxy)diethyl ether, diphenoxyxylene, bis(4-methoxyphenyl)ether, diphenyl adipate, dibenzyl oxalate, di(4-methylbenzyl)oxalate, di(4-chlorobenzyl)oxalate, dimethyl terephthalate, dibenzyl terephthalate, phenyl benzene sulfonic ester, diphenylsulfone, bis(4-allyloxyphenyl) sulfone, 4-acetylacetophenone, acetoacetic acid anilides, and fatty acid aniliides.

12. The thermal recording medium of claim 7 which is further comprised of a sensitizer.

13. The thermal recording sheet of claim 12 wherein the sensitizer is selected from the group consisting of stearamide, N-hydroxymethylstearamide, N-stearylstearamide, ethylenebisstearamide, N-stearylstearamide, ethylenebisstearamide, N-stearylurea, benzyl-2-naphthyl ether, m-terpphenyl, 4-benzylbiphenyl, 4-acetylbiphenyl, 4-(4-methylphenoxy)biphenyl, 1,2-bis(3-methylphenoxy) ethane, 1,2-diphenoxyethane, 2,2'-bis(4-methoxyphenoxy)diethyl ether, diphenoxyxylene, bis(4-methoxyphenyl)ether, diphenyl adipate, dibenzyl oxalate, di(4-methylbenzyl)oxalate, di(4-chlorobenzyl)oxalate, dimethyl terephthalate, dibenzyl terephthalate, phenyl benzene sulfonic ester, diphenylsulfone, bis(4-allyloxyphenyl) sulfone, 4-acetylacetophenone, acetoacetic acid anilides, and fatty acid anilides.

14. The thermal recording sheet of claim 7 which is further comprised of a binder.

15. The thermal recording sheet as specified in claim 14 wherein the binder is a polyvinyl alcohol.

16. The thermal recording sheet as specified in claim 14 wherein the binder is selected from the group consisting of acrylic emulsions, styrene copolymer emulsions, butadiene copolymer emulsions, acrylonitrile copolymers and terpolymer emulsions, polyvinyl acetate emulsions, vinyl acetate ethylene emulsions, polyurethane emulsions, starches, and hydroxymethyl cellulose.

17. The thermal recording sheet of claim 7 which is further comprised of a filler.

18. The thermal recording sheet of claim 17 wherein the filler is selected from the group consisting of titanium dioxide, silica, aluminum tri-hydrate, clay, mica, calcium carbonate, talc, magnesium hydroxide, magnesium oxide, hollow plastic spheres, and polystyrene.

19. The thermal recording sheet of claim 7 which is further comprised of a slip agent.

20. The thermal recording sheet of claim 19 wherein the slip agent is selected from the group consisting of zinc stearate, calcium stearate, stearamide, and polyethylene wax.

21. The thermal recording sheet of claim 7 which is further comprised of a UV absorber.

22. The thermal recording sheet of claim 7 which is further comprised of an optical brightener.

23. A thermal recording medium which is comprised of a substrate having thereon a recording layer containing a colorless or pale colored dye precursor and a color developer reactable with said dye precursor upon heating to develop a color, wherein said color developer is a compound selected from the group consisting of p-(p-{3-[p-(p-hydroxyphenoxy)phenyl]ureido}phenoxy)phenol, m-(p-{3-[p-(p-hydroxyphenoxy)phenyl]ureido}phenoxy)phenol, o-(p-{3-[p-(p-hydroxyphenoxy)phenyl]ureido}phenoxy)phenol, p-(p-{3-[m-(p-hydroxyphenoxy)phenyl]ureido}phenoxy)phenol, and p-(m-{3-[o-(p-hydroxyphenoxy)phenyl]ureido}phenoxy)phenol.

24. The thermal recording medium of claim 23 which is further comprised of an electron accepting material selected from the group consisting of 2,4'-Dihydroxydiphenylsulfone (CAS#5397-34-2), 4,4'-Dihydroxydiphenylsulfone (CAS#80-90-1), Bis-(3-allyl-4-hydroxyphenyl)sulfone (CAS#41481-66-7), 4-[4'-[(1'-methylethyloxy)phenyl]sulfonyl]phenol (CAS#191680-83-8), 4-hydroxyphenyl 4-isoprooxyphenylsulfone (CAS#95235-30-6), N-(p-Toluenesulfonyl)-N'-(3-p-toluenesulfonyloxyphenyl)urea (CAS#232938-43-1), Phenol, 4-[[4-(2-propen-1yloxy)phenyl]sulfonyl (CAS#97042-18-7), 4-Hydroxy-4'benzyloxydiphenylsulfone (CAS#63134-33-8), and 4,4'bis(N-carbamoyl-4-methylbenzenesulfonamide)diphenylmethane (CAS#151882-81-4).

25. The thermal recording medium of claim 23 wherein the colorless or pale colored dye precursor is selected from the group consisting of 2-anilino-3-methyl-6-diethylaminofluorane, 2-anilino-3-methyl-6-dibutylaminofluorane, 2-anilino-3-methyl-6-(N-ethyl-N-isoamylamino)fluorine, 2-anilino-3-methyl-6-(N-ethyl-N-propylamino)fluorane, 2-anilino-3-methyl-6-di-n-amylaminofluorane, 2-anilino-3-methyl-6-(N-ethyl-N-p-tolylamino)fluorane, 2-anilino-3-methyl-6-N-ethyl-N-sec-butylaminofluorane, 3-di-(n-pentylamino)-6-methyl-7-anilinofluorane, 3-(N-isoamyl-N-ethylamino)-6-methyl-7-anilinofluorane, 3-(N-n-hexyl-N- ethylamino)-6-methyl-7-anilinofluorane, 3-[N-(3-ethoxypropyl)-N-ethylamino]-6-methyl-7-anilinofluorane, 3-di-(n-butylamino)-7-2-chloroanilino)fluorane, 3-diethylamino-7-(2-chloroanilino)fluorane, and 3-(N-cyclohexyl-N-methylamino)-6-methyl-7-anilinofluorane.

26. The thermal recording medium of claim 23 which is further comprised of a binder.

27. The thermal recording medium as specified in claim 26 wherein the binder is a polyvinyl alcohol.

28. The thermal recording medium as specified in claim 27 wherein the binder is selected from the group consisting of acrylic emulsions, styrene copolymer emulsions, butadiene copolymer emulsions, acrylonitrile copolymers and terpolymer emulsions, polyvinyl acetate emulsions, vinyl acetate ethylene emulsions, polyurethane emulsions, starches, and hydroxymethyl cellulose.

29. The thermal recording medium of claim 23 which is further comprised of a filler.

30. The thermal recording sheet of claim 29 wherein the filler is selected from the group consisting of titanium dioxide, silica, aluminum tri-hydrate, clay, mica, calcium carbonate, talc, magnesium hydroxide, magnesium oxide, hollow plastic spheres, and polystyrene.

31. The thermal recording medium of claim 23 which is further comprised of a slip agent.

32. The thermal recording medium of claim 31 wherein the slip agent is selected from the group consisting of zinc stearate, calcium stearate, stearamide, and polyethylene wax.

33. The thermal recording medium of claim 23 which is further comprised of a UV absorber.

34. The thermal recording medium of claim 23 which is further comprised of an optical brightener.

* * * * *